United States Patent
Blomqvist et al.

(10) Patent No.: US 6,884,158 B1
(45) Date of Patent: Apr. 26, 2005

(54) PLACING UNIT FOR A HUMAN BEING

(75) Inventors: Tomas Blomqvist, Vastervik (SE); George Kinigalakis, Uppsala (SE); Per Hvåss, Tullinge (SE)

(73) Assignee: Biometron AB, Vastervik (SE)

( * ) Notice: Subject to any disclaimer, the term of this patent is extended or adjusted under 35 U.S.C. 154(b) by 0 days.

(21) Appl. No.: 09/926,128
(22) PCT Filed: Mar. 6, 2000
(86) PCT No.: PCT/SE00/00435
    § 371 (c)(1),
    (2), (4) Date: Dec. 6, 2001
(87) PCT Pub. No.: WO00/53143
    PCT Pub. Date: Sep. 14, 2000

(30) Foreign Application Priority Data

Mar. 9, 1999 (SE) .............................. 9900868

(51) Int. Cl.⁷ .............................. B08B 15/00
(52) U.S. Cl. ................. 454/66; 55/385.1; 454/189
(58) Field of Search .................. 454/49, 57, 66, 454/191, 189; 55/385.1, 385.8, 473, 472

(56) References Cited

U.S. PATENT DOCUMENTS

| | | | |
|---|---|---|---|
| 3,273,323 A | * 9/1966 | Whitfield | 55/385.2 |
| 3,505,989 A | * 4/1970 | Truhan | 600/21 |
| 3,923,482 A | * 12/1975 | Knab et al. | 55/412 |
| 4,252,054 A | 2/1981 | Bakels | |
| 4,422,369 A | 12/1983 | Smets | |
| 4,898,089 A | 2/1990 | Roos | |
| 4,909,815 A | * 3/1990 | Meyer | 96/131 |
| 5,074,198 A | * 12/1991 | Aalto et al. | 454/191 |
| 5,700,190 A | * 12/1997 | Johnson et al. | 454/57 |
| 6,010,400 A | * 1/2000 | Krainiak et al. | 454/187 |
| 6,099,607 A | * 8/2000 | Haslebacher | 55/356 |
| 6,251,006 B1 | * 6/2001 | Laborde et al. | 454/190 |

FOREIGN PATENT DOCUMENTS

| | | | | |
|---|---|---|---|---|
| DE | 3203674 | | 8/1983 | |
| DE | 3644417 | | 7/1988 | |
| GB | 904052 | * | 8/1962 | 454/66 |
| JP | 62-33231 | * | 2/1987 | 454/66 |
| JP | 62-294831 | * | 12/1987 | 454/66 |

* cited by examiner

*Primary Examiner*—Harold Joyce
(74) *Attorney, Agent, or Firm*—Dennison, Schultz, Dougherty & MacDonald

(57) ABSTRACT

In a dentist's surgery, a treatment room, and premises where different chemicals are handled or where welding or soldering is performed there are a number of pollutants. In accordance with the invention, these pollutants are removed by an endless air-jet circuit (5), which during its course passes a treatment locus as well as a filter.

1 Claim, 4 Drawing Sheets

PLACING UNIT FOR A HUMAN BEING

The present invention relates to a placing unit for a human being. Such units have special uses within the health-care industry, in medical care as well as dental care. In dental treatment, a large number of chemical products are used that have allergenic and toxic properties. These disadvantages, which pose health risks, can only be counteracted by traditional ventilation techniques based on general ventilation and some form of process ventilation. Existing installations for this purpose generally constitute an obstruction for the dental-care staff in cramped working spaces and further occasion high levels of noise. The invention can also be used in other work places where welding or soldering is performed or where other substances capable of emitting gases and pollutants are used and where there is a need to counteract health risks.

Air pollutants are encountered partly in the form of gases and partly in the form of particles. Among the gaseous substances that are found in indoor air, apart from carbon dioxide and certain exhaust fumes, volatile substances in an average concentration of up to 16 mg/m3, organic compounds in concentrations of up to 9 mg/m3, monomer vapours, acrylates, toluene, isopropanol, ethanol, isobutanol, formaldehyde, chloroform, mercury, mercury vapour, nitrous oxide and the like can be mentioned. Among the particle pollutants, particles of amalgam, microscopic mercury drops, composite particles, pollen, spores of mould, bacteria, viruses, micro-organisms, inorganic dust, particles of dirt and the like can be mentioned. Cytotoxins, toxic gases, chemicals and various other pollutants can likewise be encountered.

The present invention performs the task of directing a jet of air at the placing unit and, in particular at one or several parts of the same or at the entire unit. The unit is provided with receiving openings that guide the directed jet of air to an exhaust-suction apparatus that removes the pollutants and allows purified air to flow out and be conveyed to the device that generates said directed jet of air. On its way to the device producing the directed jet of air, the purified air can pass one or several devices for further purification of the air. These devices can also act as purifiers for the air present in the treatment area where the placing unit is located. The device that generates the directed jet of air, can be designed such that the out-flowing air is laminar and the device can further be designed such that the out-flowing air can be pulsating. The device can also regulate the temperature of the directed air jet. In addition, the present invention can be used as movable equipment within the health-care industry, as well as in other fields of work where substances emitting gases and other toxic substances are handled.

Further particulars of the present invention appear in the appended claims.

Figure 1:
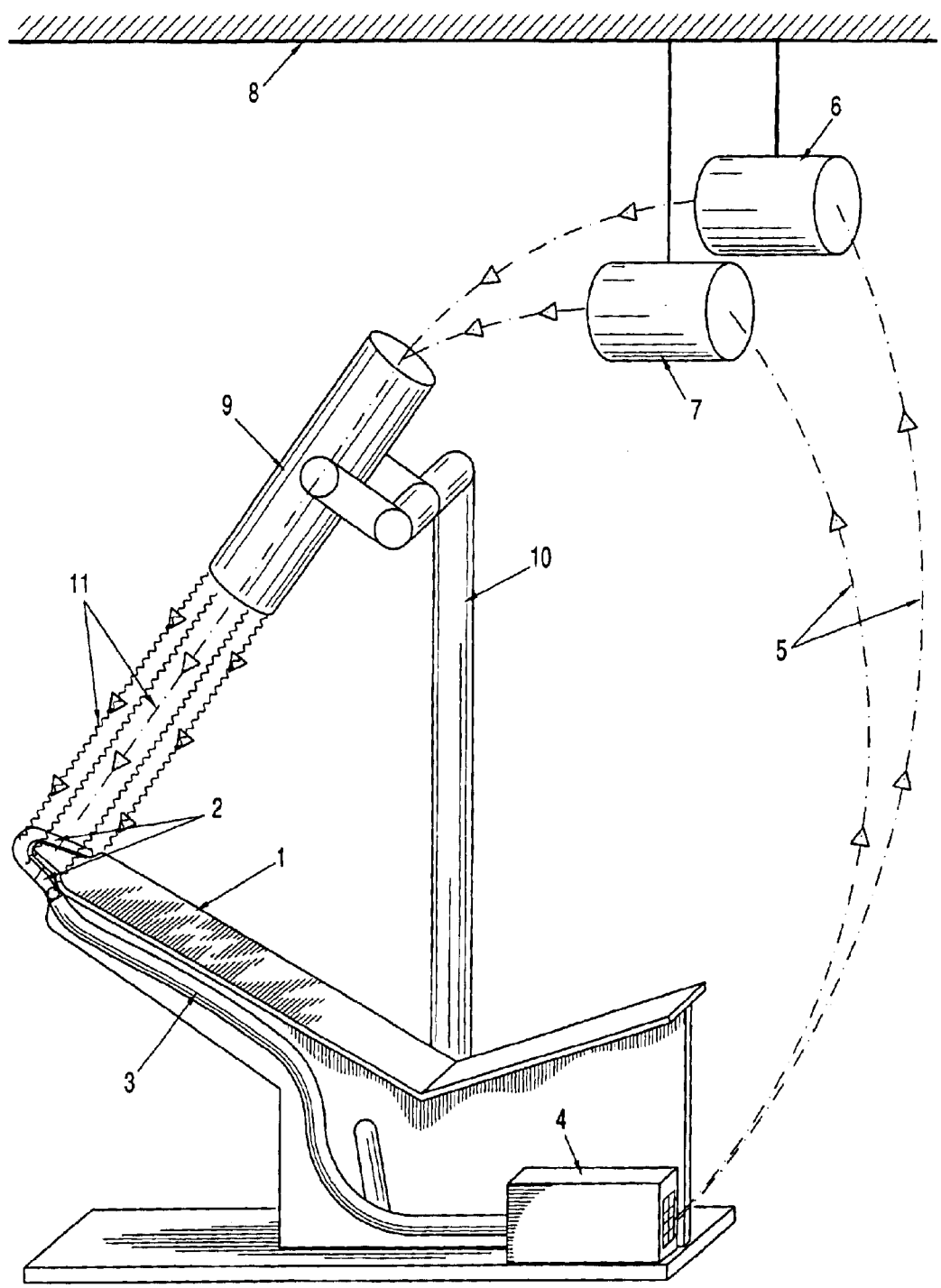
FIG. 1 shows an embodiment of the invention applied to a dentist's chair.

The number 1 designates an adjustable dentist's chair with an upper part 2 for a head. The upper part comprises receiving nozzles communicating with a tube 3 that is connected to suction equipment 4 comprising arrangements for removing particles and undesired gases. The suction equipment can obviously comprise a fan, if so required. The airflows 5 from the suction device are automatically admitted to two particle and gas purifiers 6 and 7. These gas purifiers can similarly be provided with fans and these gas purifiers are attached to the ceiling 8 of a treatment room. The device generating the directed jet of air 11 has been allocated designation number 9 and can be termed a generator or transmitter. The device 9 is mounted on a stand 10 that in one way or another is placed near the placing unit or on the floor of the treatment room. The device 9 can be directed in any desired way whatsoever and, in relation to a dentist's chair, it is suitable to direct the device 9 as shown in the drawing, that is to say such that the jet of air 11 impinges on the head of the person being treated and on the area where the dentist is working, so that the patient, as well as the dentist, is subjected to a minimum of pollutants. The device 9 comprises the members required to produce a laminar flow. Furthermore, the device can be provided with members that regulate the speed of the directed jet of air. Other devices that can be encompassed by the device 9 are pulsation members for making the directed let of air 11 pulsate and heating members for regulating the temperature of the directed jet of air 11.

Figure 2:
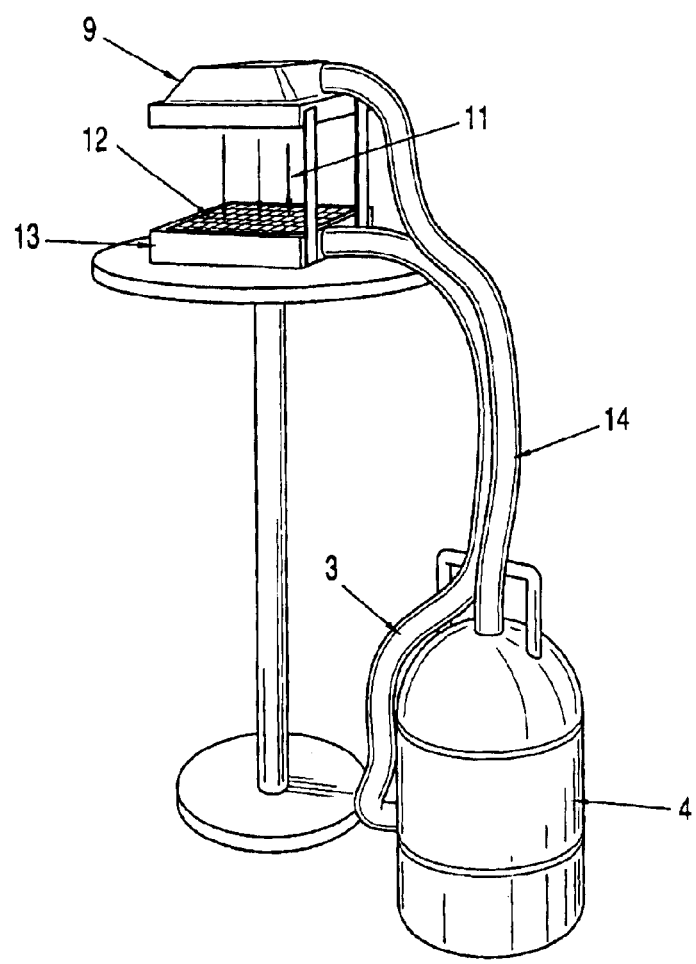
FIGS. 2, 3 and 4 show a movable embodiment of the invention.
Figure 3:
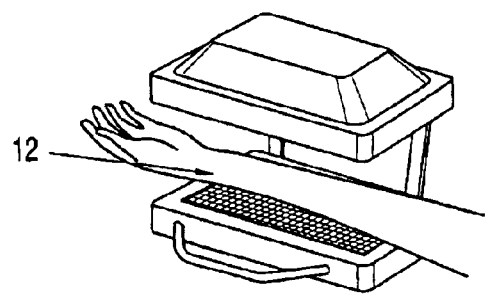
Figure 4:
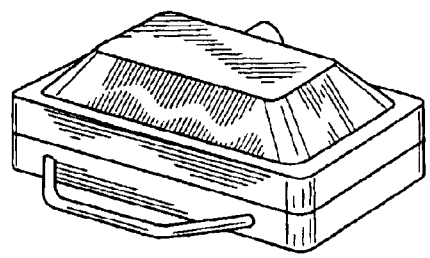
Figure 5:
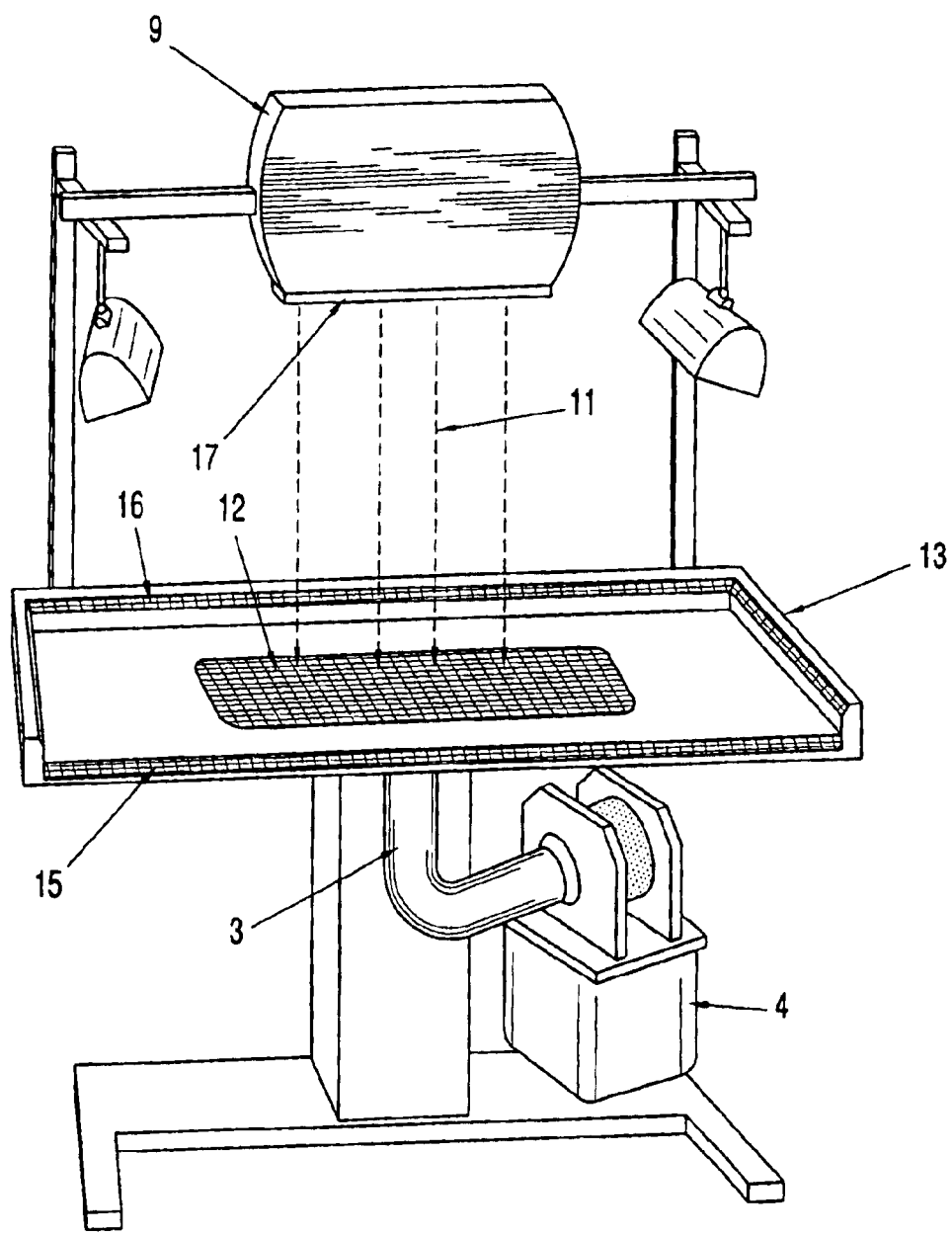
FIG. 5 shows an embodiment of the invention on a worktable.
Figure 6:
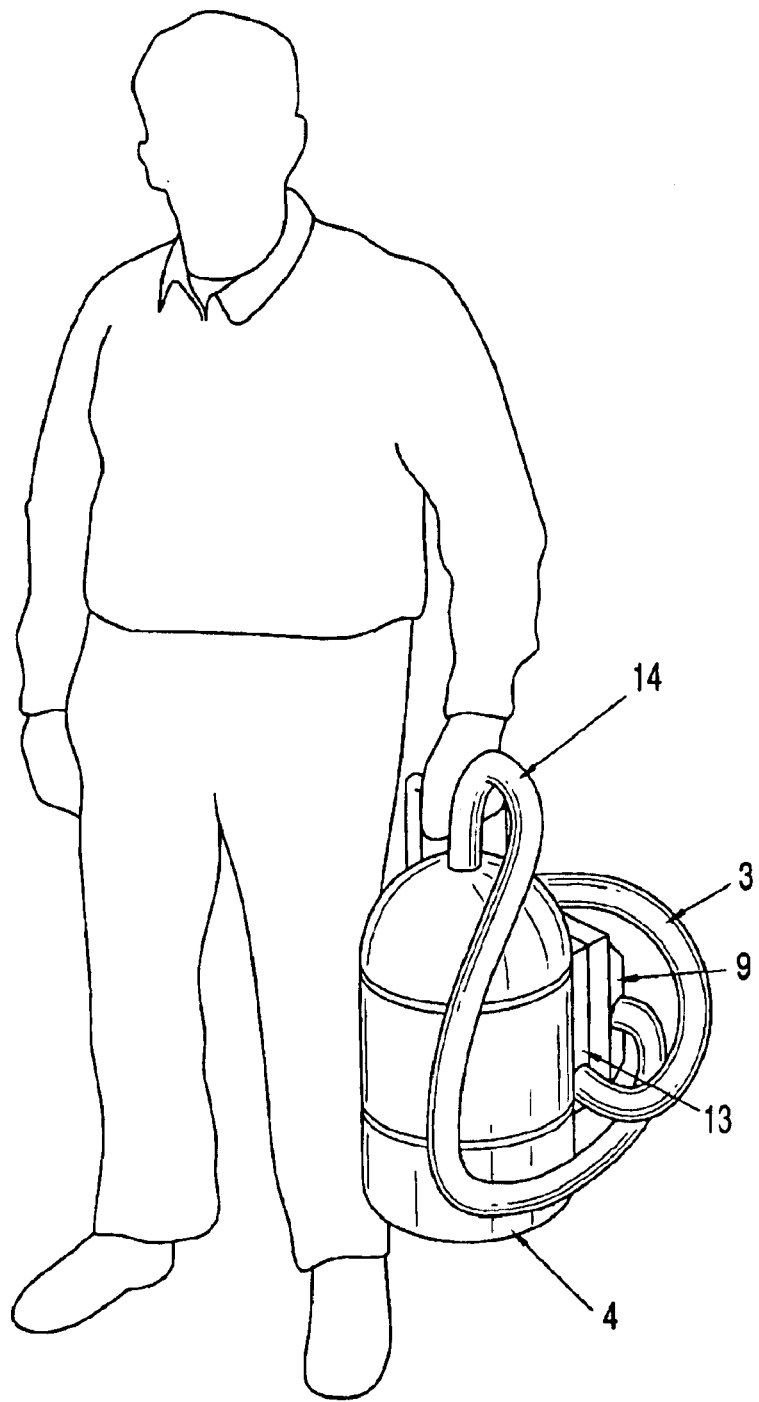
FIG. 6 shows the movable unit being transported.

As is clearly and explicitly shown in FIG. 1, the device 9 emits a laminar jet of air 11 that is directed at a patient and a working dentist. Said jet of air 11 is thereafter caused to pass through a suction device 4 and air purified in the suction device is admitted to the devices 6 and 7 for further purification. Thereafter the air is admitted to the device 9 for generating a laminar jet of air. Thus, the air utilized at the treatment locus passes in a closed circuit. It will furthermore be obvious that the devices 6 and 7 also allow the air in the treatment area to pass through them and be purified. Thus, the units 6 and 7 fulfil two functions, namely to purify the treatment air as well as the air in the treatment area. FIG. 2 shows a filter unit 4 that generates the air of the emitting means 9, which emits a laminar let of air 11 towards the receiving means 13, comprising a work surface 12 that is provided with a suction grille. The pollutants are drawn down into the filter unit 4 via the tube 3. FIG. 3 shows how the object to be treated can be placed on the work surface 12. How the emitting means 9 and the receiving means 13 can be fitted together is evident from FIG. 4. As illustrated by FIG. 5, the equipment can be used on a larger worktable, where the emitting unit 9 emits a laminar jet of air 11 down towards the receiving means 13, which consists of a work surface 12, comprising a work surface 12 provided with a suction grille. Furthermore, the receiving means 13 is provided along all its edges with edge suction 15 and 16, communicating with the receiving means 13, which in turn communicates with a suction tube 3, extending from the receiving means 13 to the suction unit 3, which is provided with a gas and particle filter. As shown in FIG. 6, the emitting means 9, the receiving means 13, the filter unit 4, and the tubes 3 and 14 can be assembled to form a movable unit. It is important to ascertain the correlation between the emitting speed of the laminar air and the receiving speed of the air that is admitted to attain the optimal emitting-receiving relationship. To obtain the best effect, the air jet should have full force up to approximately 50 mm above the receiving means, at which point it captures the flow of air. A target value for the air speed can be that the emitting speed and the receiving speed are the same.

It will be apparent that devices of the type indicated by designation number 9 can be used to obtain a jet of air directed at an operating table, at parts of the same or at the entire operating table or worktable.

What is claimed is:

1. A placing unit, comprising:

a work table having a support base and a non-perforated work surface having a plurality of airflow slots in a middle portion thereon, a peripheral edge, a plurality of airflow slots on said peripheral edge, an emitting unit supported above said work surface, said emitting unit having a plurality of vanes for providing a laminar airflow through said plurality of airflow slots on said work surface and said plurality of airflow slots on said peripheral edge, a filter screen disposed on said emitting unit, a filter unit, a suction tube having a first end and a second end, said first end of said suction tube is operatively connected to said filter unit, and said second end of said suction tube is operatively connected to said plurality of slots on said work surface and said plurality of slots on said peripheral edge.

* * * * *